United States Patent [19]

Merril

[11] Patent Number: 6,106,301
[45] Date of Patent: Aug. 22, 2000

[54] INTERVENTIONAL RADIOLOGY INTERFACE APPARATUS AND METHOD

[75] Inventor: Gregory L. Merril, Chevy Chase, Md.

[73] Assignee: HT Medical Systems, Inc., Rockville, Md.

[21] Appl. No.: 08/923,477

[22] Filed: Sep. 4, 1997

Related U.S. Application Data

[60] Provisional application No. 60/025,433, Sep. 4, 1996, abandoned.

[51] Int. Cl.$^7$ .................................................. F41G 3/26
[52] U.S. Cl. ............................................................. 434/262
[58] Field of Search ................................... 434/262, 263, 434/28

[56] References Cited

U.S. PATENT DOCUMENTS

D. 233,238  10/1974  Reid et al. .
D. 272,833   2/1984  Van Assche et al. .

(List continued on next page.)

FOREIGN PATENT DOCUMENTS

| 169-776 | 1/1986 | European Pat. Off. . |
|---|---|---|
| 0485766 | 5/1992 | European Pat. Off. . |
| 08/00804 | 10/1997 | European Pat. Off. . |
| 09/08836 | 4/1999 | European Pat. Off. . |
| 2 592 514 | 7/1987 | France . |
| 3834-553 | 4/1990 | Germany . |
| 1124-372 | 11/1984 | U.S.S.R. . |
| 1335-994 | 11/1987 | U.S.S.R. . |
| 1732371-A1 | 5/1992 | U.S.S.R. . |
| WO 93/08517 | 4/1993 | WIPO . |
| WO 95/02233 | 1/1995 | WIPO . |
| WO 95/02801 | 1/1995 | WIPO . |
| WO 96/16397 | 5/1996 | WIPO . |
| WO 96/28800 | 9/1996 | WIPO . |
| WO 98/10387 | 3/1998 | WIPO . |
| WO 98/58308 | 12/1998 | WIPO . |
| WO 99/25536 | 5/1999 | WIPO . |
| WO 99/38141 | 7/1999 | WIPO . |

OTHER PUBLICATIONS

Steven Ginsberg, This Shot Won't Hurt You at All, Article, Washington Business, Jul. 6, 1998, Washington, D.C.

Gregory Merril, Virtual and Augmented Reality in Medicine, Proceedings of the IEEE, Mar. 1998, vol. 86, No. 3, Piscataway, NJ.

J.D. Westwood, H.M. Hoffman, D. Stredney and S.J. Weghorst (Eds.), Training Environment for Inferior Vena Caval Filter Placement, Article, Medicine Meets Virtual Reality, Jan. 28–31, 1998, San Diego, California.

(List continued on next page.)

*Primary Examiner*—Jessica J. Harrison
*Assistant Examiner*—Sheila Clayton

[57] ABSTRACT

An interventional radiology interface apparatus and method interfaces peripherals in the form of mock medical instruments to a medical procedure simulation system to enable performance of a medical procedure on a virtual patient. The interface apparatus includes a guidewire, catheter and sheath, an injection syringe, an inflation syringe and a foot switch to realistically simulate the instruments utilized during an actual medical procedure. A user manipulates guidewire, catheter and sheath peripherals to traverse an arterial network toward a simulated blockage shown on the medical procedure simulation system display. The foot switch controls the display to provide a fluoroscope image showing the position of the guidewire, catheter, sheath and blockage within the arterial network. The injection syringe may be manipulated to simulate injections of contrast fluid or other pharmaceutical substances through the catheter or sheath into the virtual patient. When a guidewire is positioned past the simulated blockage within the arterial network, the catheter is exchanged for a balloon-tipped angioplasty catheter, and the inflation syringe is manipulated to simulate inflation of the balloon to reduce the blockage. In addition, the interface apparatus may apply force feedback to the guidewire and catheter to simulate forces encountered by these instruments during an actual medical procedure. The interface apparatus measures peripheral manipulation and transfers these measurements via a processor to the medical procedure simulation system to enable simulation of the medical procedure.

24 Claims, 3 Drawing Sheets

U.S. PATENT DOCUMENTS

| | | |
|---|---|---|
| D. 392,878 | 3/1998 | Nordstrom et al. . |
| 3,226,846 | 1/1966 | Wood . |
| 3,304,434 | 2/1967 | Koster . |
| 3,541,541 | 11/1970 | Engelbart . |
| 3,748,366 | 7/1973 | Rader et al. . |
| 3,775,865 | 12/1973 | Rowan . |
| 4,321,047 | 3/1982 | Landis . |
| 4,360,345 | 11/1982 | Hon . |
| 4,409,479 | 10/1983 | Sprague et al. . |
| 4,459,113 | 7/1984 | Boscaro Gatti et al. . |
| 4,490,810 | 12/1984 | Hon . |
| 4,642,055 | 2/1987 | Saliterman . |
| 4,712,101 | 12/1987 | Culver . |
| 4,726,772 | 2/1988 | Amplatz . |
| 4,767,333 | 8/1988 | Born . |
| 4,773,865 | 9/1988 | Baldwin . |
| 4,789,340 | 12/1988 | Zikria . |
| 4,804,328 | 2/1989 | Barrabee . |
| 4,807,158 | 2/1989 | Blanton et al. . |
| 4,867,685 | 9/1989 | Brush et al. . |
| 4,879,668 | 11/1989 | Cline et al. . |
| 4,907,973 | 3/1990 | Hon . |
| 4,936,862 | 6/1990 | Walker et al. . |
| 4,936,892 | 6/1990 | Walker et al. . |
| 5,044,956 | 9/1991 | Behensky et al. . |
| 5,077,608 | 12/1991 | Dubner . |
| 5,086,401 | 2/1992 | Glassman et al. . |
| 5,099,846 | 3/1992 | Hardy . |
| 5,112,228 | 5/1992 | Zouras . |
| 5,130,794 | 7/1992 | Ritchey . |
| 5,137,458 | 8/1992 | Ungs et al. . |
| 5,149,270 | 9/1992 | McKeown . |
| 5,185,561 | 2/1993 | Good et al. . |
| 5,205,289 | 4/1993 | Hardy et al. . |
| 5,220,260 | 6/1993 | Schuler . |
| 5,222,499 | 6/1993 | Allen et al. . |
| 5,261,404 | 11/1993 | Mick et al. . |
| 5,273,038 | 12/1993 | Beavin . |
| 5,295,694 | 3/1994 | Levin . |
| 5,311,422 | 5/1994 | Loftin et al. . |
| 5,320,326 | 6/1994 | Ju et al. . |
| 5,320,537 | 6/1994 | Watson . |
| 5,320,538 | 6/1994 | Baum . |
| 5,322,441 | 6/1994 | Lewis et al. . |
| 5,333,106 | 7/1994 | Lanpher et al. . |
| 5,338,198 | 8/1994 | Wu et al. . |
| 5,343,871 | 9/1994 | Bittman et al. . |
| 5,354,202 | 10/1994 | Moncrief et al. . |
| 5,376,007 | 12/1994 | Zirm . |
| 5,377,116 | 12/1994 | Wayne et al. . |
| 5,385,474 | 1/1995 | Brindle . |
| 5,389,865 | 2/1995 | Jacobus et al. . |
| 5,391,081 | 2/1995 | Lampotang et al. . |
| 5,403,191 | 4/1995 | Tuason . |
| 5,414,337 | 5/1995 | Schuler . |
| 5,438,529 | 8/1995 | Rosenberg et al. . |
| 5,451,924 | 9/1995 | Massimino et al. . |
| 5,454,722 | 10/1995 | Holland et al. . |
| 5,459,382 | 10/1995 | Jacobus et al. . |
| 5,482,472 | 1/1996 | Garoni et al. . |
| 5,483,254 | 1/1996 | Powell . |
| 5,483,961 | 1/1996 | Kelly et al. . |
| 5,509,810 | 4/1996 | Schertz et al. . |
| 5,510,832 | 4/1996 | Garcia . |
| 5,513,992 | 5/1996 | Refait . |
| 5,518,406 | 5/1996 | Waters . |
| 5,531,227 | 7/1996 | Schneider . |
| 5,546,943 | 8/1996 | Gould . |
| 5,552,995 | 9/1996 | Sebastian . |
| 5,559,412 | 9/1996 | Schuler . |
| 5,576,727 | 11/1996 | Rosenberg et al. . |
| 5,589,854 | 12/1996 | Tsai . |
| 5,593,306 | 1/1997 | Kohnke . |
| 5,609,485 | 3/1997 | Bergman et al. . |
| 5,623,582 | 4/1997 | Rosenberg . |
| 5,629,594 | 5/1997 | Jacobus et al. . |
| 5,666,138 | 9/1997 | Culver . |
| 5,682,886 | 11/1997 | Delp et al. . |
| 5,687,259 | 11/1997 | Linford . |
| 5,691,898 | 11/1997 | Rosenberg et al. . |
| 5,701,140 | 12/1997 | Rosenberg et al. . |
| 5,704,791 | 1/1998 | Gillio . |
| 5,721,566 | 2/1998 | Rosenberg et al. . |
| 5,722,836 | 3/1998 | Younker . |
| 5,724,264 | 3/1998 | Rosenberg et al. . |
| 5,731,804 | 3/1998 | Rosenberg . |
| 5,734,373 | 3/1998 | Rosenberg et al. . |
| 5,739,811 | 4/1998 | Rosenberg et al. . |
| 5,740,802 | 4/1998 | Nafis et al. . |
| 5,742,278 | 4/1998 | Chen et al. . |
| 5,755,577 | 5/1998 | Gillio . |
| 5,766,016 | 6/1998 | Sinclair et al. ........................ 434/262 |
| 5,767,839 | 6/1998 | Rosenberg . |
| 5,768,134 | 6/1998 | Swaelens et al. . |
| 5,769,640 | 6/1998 | Jacobus et al. ........................ 434/262 |
| 5,791,908 | 8/1998 | Gillio . |
| 5,800,177 | 9/1998 | Gillio . |
| 5,800,178 | 9/1998 | Gillio . |
| 5,800,179 | 9/1998 | Bailey . |
| 5,805,140 | 9/1998 | Rosenberg et al. . |
| 5,807,115 | 9/1998 | Hu . |
| 5,821,920 | 10/1998 | Rosenberg et al. . |
| 5,825,308 | 10/1998 | Rosenberg . |
| 5,825,941 | 10/1998 | Linford et al. . |
| 5,828,197 | 10/1998 | Martin et al. . |
| 5,853,292 | 12/1998 | Eggert et al. . |
| 5,873,731 | 2/1999 | Prendergast . |
| 5,873,732 | 2/1999 | Hasson . |
| 5,880,976 | 3/1999 | DiGioia, III et al. . |
| 5,882,206 | 3/1999 | Gillio .................................... 434/262 |
| 5,882,207 | 3/1999 | Lampotang et al. . |
| 5,890,908 | 4/1999 | Lampotang et al. . |
| 5,891,131 | 4/1999 | Rajan et al. . |
| 5,909,380 | 6/1999 | Dubois et al. . |
| 5,941,710 | 8/1999 | Lampotang et al. . |
| 5,945,056 | 8/1999 | Day et al. . |
| 5,947,743 | 9/1999 | Hasson . |
| 5,951,301 | 9/1999 | Younker . |
| 5,956,040 | 9/1999 | Asano et al. . |
| 5,967,790 | 10/1999 | Strover et al. . |
| 5,995,738 | 11/1999 | DiGioia, III et al. . |

OTHER PUBLICATIONS

Gary Taubes, Surgery in Cyberspace, Article, Discover, Dec. 1994.

Immersion Human Interface Corporation, "Programmer's Technical Reference Manual; Immersion PROBE and Personal Digitizer", May, 1994, pp. 1–80.

Kegier, "Surgeons Turn to Surgical Simulation Via Virtual Reality to Practive New Procedures," Laparoscopy News, Nov. 1994, pp. 6–8.

Merril et al, "Cyber Surgery: Cutting Costs, Sewing Benefits, " Virtual Reality Special Report, Summer 1994, pp. 39–42.

Hon, "Realistic Medical Simulations," Virtual Reality World, Jul./Aug. 1994, 94, pp. 59–62.

Satava, "The Role of Virtual Reality in Medicine of the 21st Century," Virtual Reality Systems, vol. 1, No. 2, Fall 1993, pp. 64–67.

Merril et al. "Virtual Heart Surgery: Trade Show and Medical Education," Virtual Reality World, Jul./Aug. 1994, pp. 55–57.

Merril et al, "Virtual Reality for Tradeshows and Individual Physician Training," Virtual Reality Systems, Spring 1994, pp. 40–44.

Rosenberg, "Medical Applications of Virtual Reality, " Virtual Reality Systems, vol. 1, No. 3, Spring 1994, pp. 48–50.

Merril et al, "Surgical Simulation Using Virtual Reality Technology: Design, Implementation, and Implications," Surgical Technology International III, Fall 1994, pp. 53–60.

Taubes, "Surgery in Cyberspace," Discover, Dec. 1994, pp. 85–94.

Krueger et al, "The Responsive workbench," IEEE Computer Graphics and Applications, May 1994, pp. 12–15.

Jackson et al, "Force Feedback and Medical Simulation," Interactive Technology and the New Paradigm for Healthcare, Jan. 1995, pp. 147–151.

Cover et al, "Interactively Deformable Models for Surgery Simulation," IEEE Computer Graphics & Applications, vol. 13, No. 6, Nov. 1993, pp. 68–75.

Okie, "Out of Body Medicine", Washington Post, Nov. 5, 1996, pp. 12–14, 17.

Smith, "Scanning the Technology", Proceedings of IEEE, vol. 86, No. 3, Mar. 1998, pp. 474–478.

Dawson et al, "The Imperitive for Medical Simulation", Proceedings of IEEE, vol. 86, No. 3, Mar. 1998, pp. 479–483.

Satava et al, "Current and Future Applications of Virtual Reality for Medicine," Proceedings of IEEE, vol. 86, No. 3, Mar. 1998, pp. 484–489.

Bro–Nielsen, "Finite Element Modeling in Surgery Simulation", Proceedings of IEEE, vol. 86, No. 3, Mar. 1998, pp. 490–503.

Ackerman, "The Visible Human Project", Proceedings of IEEE, vol. 86, No. 3, Mar. 1998, pp. 504–511.

Delingette, "Toward Realistic Soft Tissue Modeling in Medical Simulation" Proceedings of IEEE, vol. 86, No. 3, Mar. 1998, pp. 512–523.

Chan et al, "Force Feedback for Surgical Simulation", Proceedings of IEEE, vol. 86, No. 3, Mar. 1998, pp. 524–530.

Soferman et al, "Advanced Graphics Behind Medical Virtual Reality: Evolution of Algorithms, Hardware, and Software Interfaces", Proceedings of IEEE, vol. 86, No. 3, Mar. 1998, pp. 531–554.

Shahidi et al, "Clinical Applications of Three Dimensional Rendering of Medical Data Sets", Proceedings of IEEE, vol. 86, No. 3, Mar. 1998, pp. 555–568.

Hill et al, "Telepresene Technology in Medicine; Principles and Applications", Proceedings of IEEE, vol. 86, No. 3, Mar. 1998, pp. 569–580.

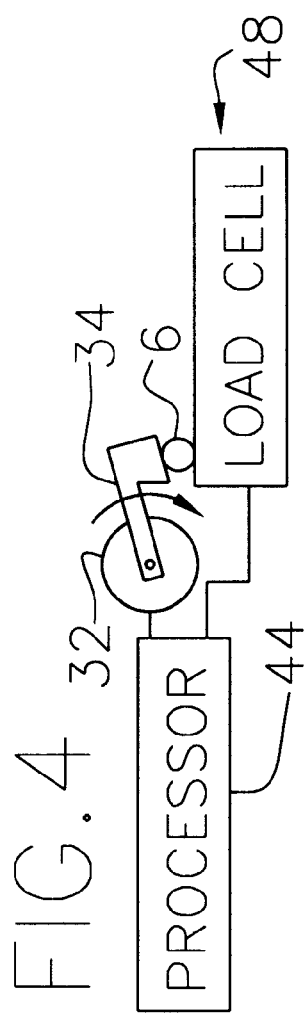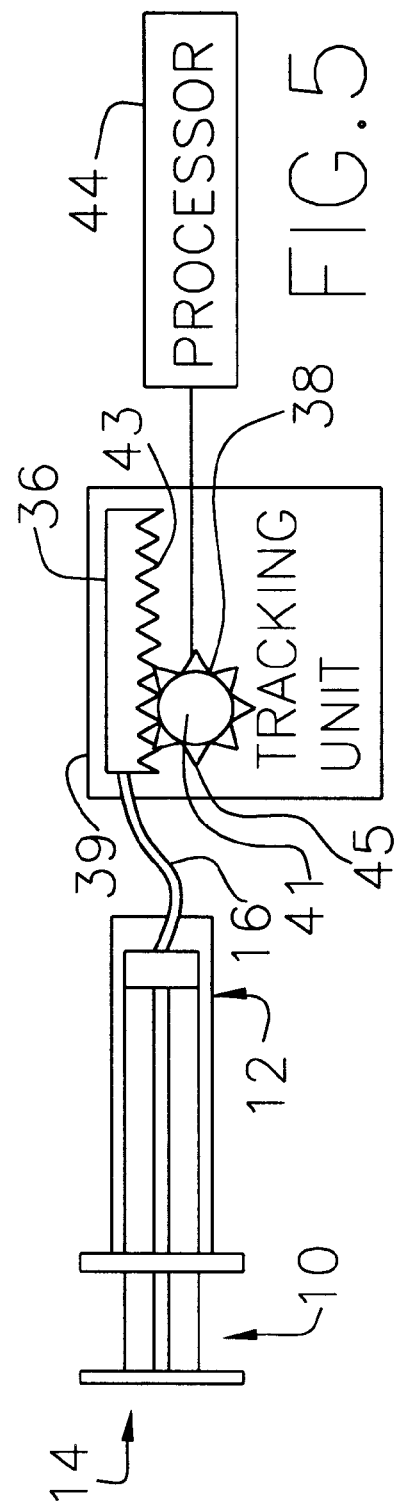

INTERVENTIONAL RADIOLOGY INTERFACE APPARATUS AND METHOD

CROSS-REFERENCE TO RELATED APPLICATIONS

This application claims priority from U.S. Provisional Patent Application Ser. No. 60/025,433, filed Sep. 4, 1996, now abandoned entitled "Interventional Radiology Interface Apparatus and Method". The disclosure of that provisional patent application is incorporated herein by reference in its entirety.

BACKGROUND OF THE INVENTION

1. Technical Field

The present invention pertains to improvements in computerized simulation systems, typically of the type disclosed in U.S. patent application Ser. No. 08/401,507, filed Mar. 10, 1995, that corresponds to International Publication Number WO 96/28800, published Sep. 19, 1996, both of which are entitled "Computer Based Medical Procedure Simulation System", and the disclosures of which are incorporated herein by reference in their entireties. In particular, the present invention pertains to an interventional radiology interface device for a computerized medical procedure simulation system, the interface device including peripherals in the form of mock medical instruments for use by a physician in performing various steps of a medical procedure in order to provide an enhanced realistic simulation of that procedure.

2. Discussion of Related Art

Generally, minimally invasive surgical procedures, such as interventional radiological procedures, may be utilized by physicians to accomplish tasks that would otherwise require a patient to undergo open surgery. For example, an angioplasty-balloon procedure may be utilized by physicians to open and eliminate blockages in a blood vessel without subjecting a patient to open heart surgery. Briefly, in the actual angioplasty-balloon procedure, a variety of changeable guidewires, catheters and sheaths are inserted into a patient and manipulated through the patient's arterial network until reaching the point where a blockage occurs. The guidewire is disposed within the catheter which, in turn, is disposed within the sheath. Navigation of these components through the arterial network is aided by a fluoroscope display showing the positions of these radiopaque instruments within the arterial network. Upon reaching the blockage point, a contrasting fluid is injected into the patient, permitting the blockage to be viewed on the fluoroscope display. The catheter is changed to an angioplasty catheter with a balloon disposed at its distal end which is centered in the blockage region and inflated to compress the blockage material on the artery walls and open the blood passageway. Balloon inflation is viewed on the display to confirm that the balloon is appropriately inflated to eliminate the blockage without rupturing the artery walls.

Performance of minimally invasive surgical procedures, such as interventional radiological procedures, requires great skill to avoid complications that may cause serious injury to a patient and/or require the patient to undergo open surgery. For example, in an angioplasty-balloon procedure, the physician is required to navigate a guidewire, catheter and sheath through an arterial network to a blockage point and inflate a balloon to eliminate the blockage as described above while avoiding a number of possible complications, such as rupturing an artery wall or dissecting the wall of the artery. Thus, physicians need to acquire the necessary skill levels and experience to perform minimally invasive surgical procedures in order to ensure successful performance of these types of procedures on patients. Although practicing minimally invasive surgical procedures on live patients provides excellent training, a procedure may usually only be performed once on a particular live patient and typically requires the presence of a skilled physician to supervise and oversee the procedure to avoid serious injury to the patient. Further, training physicians or other medical professionals in minimally invasive surgical procedures on live patients requires the use of proper facilities and equipment (e.g., hospital facilities and equipment), thereby incurring substantial costs and limiting procedure practice to a particular time and location. Moreover, since only one physician is able to practice a procedure on a particular live patient, the quantity of physicians that may practice or perform minimally invasive surgical procedures is severely restricted, thereby limiting the quantity of physicians that may acquire sufficient experience to perform these types of procedures.

The prior art has attempted to overcome the above described disadvantages of utilizing live patients to train physicians or other medical professionals to perform various minimally invasive surgical procedures by employing simulation techniques. In particular, U.S. Pat. No. 4,907,973 (Hon) discloses an expert system simulator for modeling realistic internal environments. The simulator may be utilized to simulate an angioplasty-balloon operation wherein a mock catheter is inserted and manipulated within an internal arterial modeling device. The internal arterial modeling device may include mock arterial paths with sensors to track the progress of the inserted catheter within those paths. A computer retrieves and processes data from storage based on sensor data received from the internal sensors, and sends the processed data to a display that provides a visual display simulating a realistic environment (e.g., a view of the catheter within an arterial network).

U.S. Pat. No. 4,642,055 (Saliterman) discloses a hemodynamic monitoring training system that allows medical professionals to obtain substantial experience in hemodynamic monitoring (i.e., placement of a catheter passed from a distant vein through the heart to the pulmonary vasculature for purposes of measuring intracardiac, pulmonary artery and wedge pressures to determine the type or extent of cardiopulmonary disease, to evaluate therapeutic measures and to monitor cardiac function). The system includes a trainer, computer, display, keyboard and mouse and simulates the catheterization process. A catheter having a balloon disposed at its distal end is inserted within a trainer manikin at a catheter insertion point. The balloon is typically inflated to assist the catheter tip through the heart, and may be inflated in the pulmonary artery to measure wedge pressure. The manikin includes tubes representing veins extending internally from the insertion points, and a position sensor that measures advancement of the catheter tip past the sensor. The sensor data enables the computer to determine the location of the catheter tip within a corresponding actual human body based on catheter manipulation within the trainer manikin. The computer receives signals from the trainer and may provide on the display a simulated fluoroscope image showing simulated movement of the catheter through the heart and vasculature.

The Hon and Saliterman systems suffer from several disadvantages. Specifically, these systems utilize a physical model, thereby restricting training of a medical procedure to a particular bodily region or arterial paths defined by that model. Further, use of physical models degrades realism of the simulation and reduces the benefits of simulation training since the models usually do not contain substantially the same complex anatomy as an actual body, and permit a physician or other medical professional to become accustomed to performing a procedure on the same model anatomy. Performance of the procedure on another bodily region or through different arterial paths within the Hon and Saliterman systems typically requires a new model or substantial modifications to an existing model, thereby limiting flexibility of the systems and increasing system costs. Moreover, the Saliterman system does not provide computer-controlled force feedback to an instrument, thereby degrading realism of the simulation and reducing the benefits of simulation training. In other words, the Saliterman system does not provide a computer simulated feel of forces applied to an instrument during an actual medical procedure.

In order to overcome the disadvantages of utilizing physical models described above, medical procedure simulation systems employ virtual reality technology to simulate performance of a medical procedure on a virtual bodily region of interest. Various types of interface devices are typically utilized by these systems to enable a user to interact with the simulation system. In addition, the interface devices may provide force feedback to the user to simulate the forces encountered during an actual medical procedure. For example, International Publication Number WO 95/02233 (Jacobus et al) discloses a medical procedure simulation system that utilizes virtual reality technology and force feedback to provide an accurate simulation of endoscopic medical procedures. The system includes a display device, sound device, graphics/image processing engine and storage module and programmable tactile/force reflecting mechanisms (e.g., disposed within an interface device) that provide force feedback to generate the "feel" of medical instruments and the interaction of the instruments with an anatomical simulation. Force feedback is typically accomplished by a tactile/force reflecting mechanism via a four axis device that imparts forces and torques to a user's hands through a member representative of a medical instrument in response to manipulation of that member. The forces and torques are applied to the user's hands based on the position of the member in relation to characteristics of a geometric model of an organ or virtual reality simulation of a medical procedure environment. The forces and torques are typically generated by four servomotors that manipulate the member to provide a realistic feel during simulation.

U.S. Pat. No. 5,623,582 (Rosenberg) discloses a human/computer interface tool, typically for use with virtual reality simulation systems. The interface tool preferably interfaces a substantially cylindrical object, such as a shaft of a surgeon's tool, to a simulation system computer such that the computer may generate signals to provide a virtual reality simulation with force feedback applied to the object. The interface tool includes a gimbal mechanism having two degrees of freedom coupled to a support, and preferably three electromechanical transducers. The object, when engaged by the gimbal mechanism, may move with three degrees of freedom within a spherical coordinate space wherein each transducer is associated with and senses a respective degree of freedom of motion of the object. A fourth transducer may be utilized by the interface tool to measure rotation of the object about an axis. Alternatively, the interface tool may accommodate catheter insertion virtual reality systems, typically utilizing catheters having two degrees of freedom of motion, wherein the interface tool includes two transducers that are associated with and sense translation and rotation of a catheter, respectively. The transducers of the interface tool may include actuators to impart a force upon the object to provide force feedback to a user.

Another computer interface device for surgical simulation systems includes the Immersion PROBE produced by Immersion Corporation of Palo Alto, Calif. This interface device includes a pen-like stylus supported on a light-weight mechanical linkage having six degrees of freedom, and reports the position and orientation of the stylus to a computer via a serial port interface. Sensors are disposed at the linkage joints and send spatial coordinates (i.e., X, Y, Z) and orientation (i.e., roll, pitch, yaw) of the stylus to the computer.

The interface devices described above suffer from several disadvantages. In particular, the Jacobus system and tactile/force reflecting mechanisms are primarily directed toward simulation of endoscopic medical procedures and their associated instruments, and are typically not suited for accommodating medical procedures utilizing other types of instruments. Force feedback is accomplished within each Jacobus system tactile/force reflecting mechanism (e.g., disposed within an interface device) by a four axis device having several servomotors to generate the force feedback for only a single instrument, thereby increasing system complexity and cost. The Rosenberg interface tool typically may only accommodate a single instrument, thereby limiting the interface tool to simulation of only those medical procedure steps utilizing that instrument. Further, the Rosenberg interface tool typically may only accommodate an instrument having an elongated shaft, thereby limiting the interface tool to simulation of procedures or procedure steps that utilize a particular type of instrument compatible with the interface tool. Moreover, the Rosenberg interface tool includes a plurality of actuators to provide force feedback to only a single instrument, thereby increasing system complexity and cost. In addition, the Jacobus and Rosenberg interface devices described above each typically accommodate a limited quantity of instruments or a specific type of instrument for medical procedure simulation, thereby degrading realism of the simulation and reducing the benefits of simulation training since a physician or other medical professional may only gain experience for portions of a medical procedure utilizing particular instruments.

The interface device manufactured by Immersion Corporation does not resemble a common medical instrument and does not provide a manner to apply computer controlled force feedback to the interface device, thereby degrading realism of a simulation and reducing benefits of simulation training.

U.S. patent application Ser. No. 08/401,507 discloses a computer based medical simulation system including an interface device that attempts to overcome the disadvantages described above by enabling simulation of various aspects of a medical procedure. Specifically, the system simulates a variety of medical procedures, particularly catheter based procedures, such as an angioplasty-balloon procedure, and typically includes a catheter interface device that tracks a catheter wire and sends a signal to a computer to display movement of a virtual catheter within a virtual arterial network. A user manipulates the catheter wire during simulation of a medical procedure toward an occlusion in the arterial network wherein the computer generates signals to provide tactile feedback force to the catheter wire. The system may simulate other aspects of a medical procedure via a foot switch that is interfaced by the catheter interface device to enable simulation of injection of a drug, release of a contrast material for visualization of coronary arteries, and inflation of a virtual catheter balloon to remove the occlusion.

The system disclosed in U.S. patent application Ser. No. 08/401,507 may stand some improvement. Although this system simulates additional aspects of a medical procedure, such as drug injection, release of contrast material, and catheter balloon inflation, these aspects are enabled by a foot switch as opposed to the medical instruments normally utilized to perform these steps in an actual medical procedure. Thus, it is desirable to enhance realism of a simulated medical procedure and provide enhanced training of a medical procedure to physicians and other medical professionals by incorporating additional peripherals in the form of mock medical instruments into an interface device utilized by medical procedure simulation systems to enable realistic simulation of various aspects of a medical procedure.

OBJECTS AND SUMMARY OF THE INVENTION

Accordingly, it is an object of the present invention to enhance realism within a medical procedure simulation system by incorporating various peripherals in the form of mock medical instruments within an interface device utilized by the medical procedure simulation system to enable realistic simulation of various aspects of a medical procedure.

It is another object of the present invention to provide enhanced training of a medical procedure to physicians and other medical professionals by incorporating various peripherals in the form of mock medical instruments within an interface device utilized by a medical procedure simulation system to enable the physician to simulate performance of a substantial portion of a medical procedure with medical instruments commonly utilized during performance of the actual medical procedure.

Yet another object of the present invention is to enhance realism within a medical procedure simulation system and to provide enhanced training of a medical procedure to physicians and other medical professionals by incorporating a guidewire, catheter and sheath within an interface device utilized by the medical procedure simulation system to enable realistic simulation of navigation of these instruments through an arterial network.

Still another object of the present invention is to enhance realism within a medical procedure simulation system and to provide enhanced training of a medical procedure to physicians and other medical professionals by incorporating a syringe within an interface device utilized by the medical procedure simulation system to enable realistic simulation of injecting fluids within a patient.

A further object of the present invention is to enhance realism within a medical procedure simulation system and to provide enhanced training of a medical procedure to physicians and other medical professionals by incorporating a balloon inflation syringe within an interface device utilized by the medical procedure simulation system to enable realistic simulation of inflating a balloon in simulated angioplasty and stent deployment.

The aforesaid objects are achieved individually and in combination, and it is not intended that the present invention be construed as requiring two or more of the objects to be combined unless expressly required by the claims attached hereto.

According to the present invention, an interventional radiology interface apparatus and method for use with a computerized medical procedure simulation system, typically including a computer system and display, serve to interface peripherals in the form of mock medical instruments to the medical procedure simulation system computer to enable simulation of medical procedures. The interface apparatus or device includes a guidewire, catheter and sheath nested within each other, an injection syringe, a balloon inflation syringe, and a foot switch. Each of the above described interface device components is manipulable by a user to enable performance of a simulated medical procedure, typically an interventional radiological procedure, such as an angioplasty-balloon procedure. The guidewire, catheter and sheath are manipulated to traverse a virtual arterial network shown on the medical procedure simulation system display during simulation of a medical procedure. Tracking units, associated with the guidewire, catheter and sheath, are disposed within the interface device to measure translational and rotational motion of these instruments to enable the medical procedure simulation system computer to update the position of the guidewire, catheter and sheath within the virtual arterial network. The tracking units each typically include a tracking ball disposed in frictional relation with an associated instrument and a pair of rollers wherein each roller interfaces a corresponding optical encoder to respectively measure translational and rotational motion of the associated instrument. Alternatively, the tracking units may measure motion of an associated instrument via optics. In particular, each tracking unit may include a grid that surrounds the associated instrument wherein the grid includes orthogonally arranged lines and alternating reflective spaces. The associated instrument includes orthogonally arranged transducers that receive light reflected from the grid spaces and generate electrical signals in response to translational and rotational motion of the associated instrument. Further, tactile feedback units, associated with the guidewire and catheter, are disposed within the interface device to impart forces on these instruments to realistically simulate forces encountered during an actual medical procedure. The tactile feedback units each typically include a servomotor that manipulates a pressure application arm to apply force to an associated instrument. The associated instrument is disposed within the tactile feedback unit proximate a load cell that measures the force exerted on the associated instrument. The force measurement is utilized by a feedback control loop to control the amount of force applied by the servomotor and pressure application arm to the associated instrument.

The injection syringe is manipulated to simulate injections of contrast fluid or other pharmaceutical substances, typically through the sheath or catheter, into a bodily region of interest. A tracking unit, associated with the injection syringe, is disposed within the interface device to measure syringe manipulation. The syringe tracking unit typically includes a rack gear and corresponding pinion interfacing an optical encoder to measure syringe manipulation. A cable extends from the distal end of an injection syringe plunger to the rack gear wherein manipulation of the injection syringe enables the cable to initiate rack gear motion. The optical encoder measures pinion rotation in response to rack gear motion, thereby providing a measurement of injection syringe manipulation. The injection syringe manipulation measurement enables the medical procedure simulation system computer to simulate an injection of a corresponding quantity of fluid into the bodily region of interest. The foot switch is actuated to enable display of a fluoroscope image on the medical procedure simulation system display showing a blockage within the virtual arterial network subsequent to simulated injection of contrast fluid.

The balloon inflation syringe is manipulated to simulate inflation of a guidewire balloon to eliminate the blockage within the virtual arterial network. The inflation syringe is connected to a balloon that is placed within a strain gauge disposed within the interface device wherein manipulation of the balloon inflation syringe inflates the balloon. The strain gauge measures pressure exerted on the strain gauge by inflation of the balloon or, in other words, the strain gauge measures the amount of balloon inflation. The balloon inflation measurement enables the medical procedure simulation system computer to simulate inflation of a guidewire balloon within the virtual arterial network shown on the display.

In addition, a processor is disposed within the interface device to implement the feedback control loop to control the respective tactile feedback unit servomotors and to transfer measurements to and receive control signals from the medical procedure simulation system computer.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

BRIEF DESCRIPTION OF THE DRAWINGS

FIG. 4 is a side view in elevation of a tactile feedback unit applying pressure to a catheter to simulate resistance encountered during actual traversal of a catheter through an arterial network according to the present invention.

FIG. 5 is a side view in elevation of an injection tracking unit for measuring syringe manipulation in order to simulate an amount of fluid being injected into the internal bodily region of interest during an interventional radiologic procedure according to the present invention.

DESCRIPTION OF THE PREFERRED EMBODIMENTS

Figure 1:
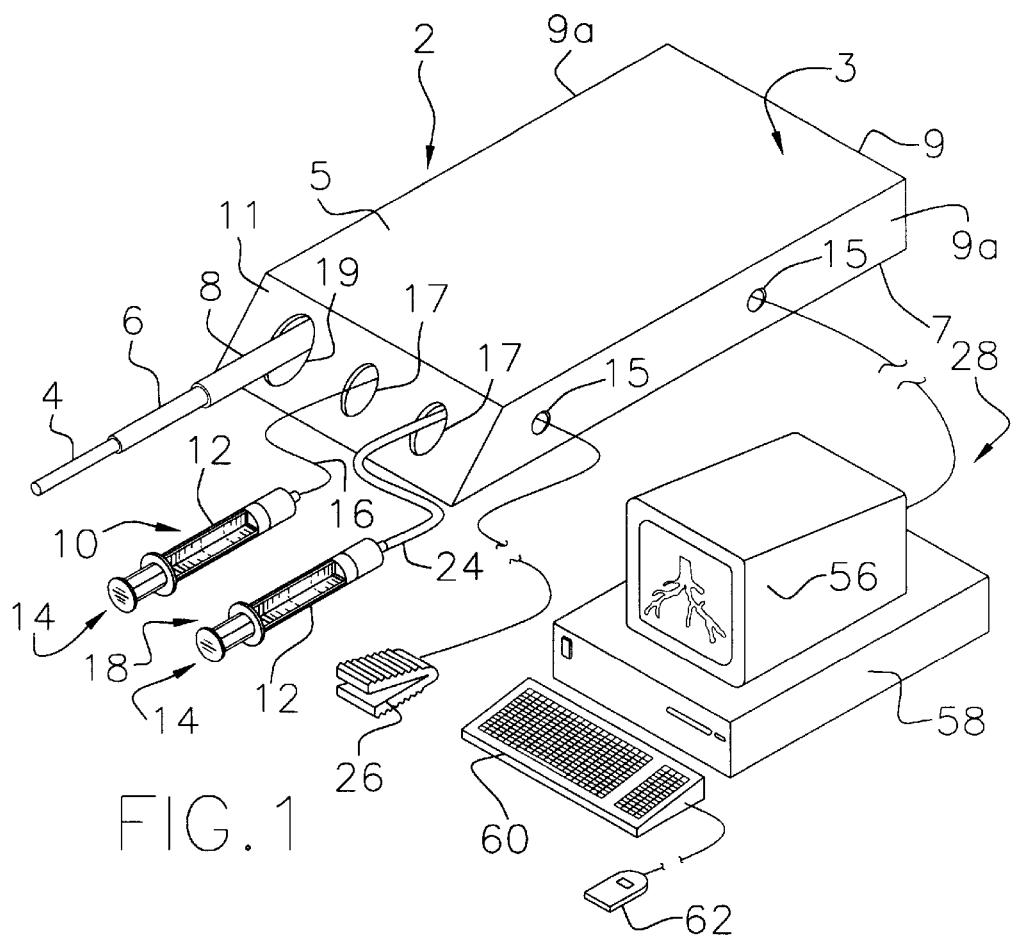
FIG. 1 is a view in perspective of a computerized medical procedure simulation system having an interventional radiology interface device with peripherals in the form of mock instruments for performing interventional radiologic procedure simulations according to the present invention.

An overall system for simulating interventional radiologic and/or other medical procedures is illustrated in FIG. 1. This medical procedure simulation system is similar to the system disclosed in U.S. patent application Ser. No. 08/401,507 except that the medical procedure simulation system includes a modified interface device having additional peripherals in the form of mock medical instruments enabling realistic simulation of various aspects of a medical procedure as described below. Specifically, an interventional radiology interface device 2 is connected to computer system 28 preferably including a monitor 56, base 58 (i.e., the processor(s), memories and accompanying hardware), keyboard 60 and mouse 62. Computer system 28 is typically a conventional or commercially available workstation, such as an Indigo2IMPACT and monitor manufactured by Silicon Graphics, Inc., and simulates, via software, an interventional radiologic or other medical procedure while displaying the particular internal bodily region of interest (e.g., an arterial network or tree) on monitor 56. The simulation display preferably emulates a fluoroscopic display commonly used in actual medical (i.e., surgical) procedures. Interface device 2 includes several peripherals in the form of mock medical instruments commonly used in interventional radiologic procedures (i.e., guidewire 4, catheter 6, sheath 8, syringes 10, 18 and foot switch 26). The device peripherals are disposed at the distal end of the interface device such that they can be manipulated during a simulation in order to perform various steps of an interventional radiologic procedure. The device peripherals are substantially similar to, and function in a similar manner as, the corresponding instruments commonly used in interventional radiologic procedures. During simulation of an interventional radiologic procedure, monitor 56 displays the internal bodily region of interest (e.g., an arterial network or tree), and adjusts the display to reflect the effects of manipulating the peripheral devices. For example, the display may show a guidewire traversing through an arterial tree as the guidewire peripheral is manipulated. In other words, the display essentially reflects the motion of the guidewire peripheral such that movement of the peripheral alters the guidewire position on the display. Thus, an interventional radiologic procedure is simulated by performing the procedure steps, via manipulation of the device peripherals, based on the monitor display.

Interface device 2 is typically encased in a housing 3 having a selectively removable cover 5, a substantially rectangular base 7 parallel to cover 5, a plurality of walls 9 extending substantially perpendicular from base 7, and a substantially rectangular tilted wall 11. Base 7 is oriented substantially horizontally such that the base length (i.e., the longer dimension of the base) extends between the proximal end and distal end (i.e., the end where the device peripherals are disposed) of interface device 2. The base length is approximately twice the base width. Rear wall 9 and side walls 9a extend substantially perpendicular from each of the respective peripheral edges of base 7 (i.e., each wall extends upwardly from the base) except for the front wall 11, to a height of approximately one-sixth the base length. Rear wall 9 extends between the rear edges of cover 5 and base 7 and along the entire width of the base, while side walls 9a are substantially right trapezoidal and extend from rear wall 9 to front wall 11. The edges of rear wall 9 that intersect side walls 9a are perpendicular to base 7. The forward edges of side walls 9a slope upwardly from base 7 at an angle of approximately thirty degrees to define the slope of front wall 11. Front wall 11 extends along the entire width of base 7 between the forward edges of cover 5 and base 7. Cover 5 is substantially rectangular and is disposed substantially parallel to base 7 at the top edges of walls 9, 9a and 11. Cover 5 may be removably secured to walls 9, 9a and 11 by any conventional fastening devices permitting selective removal of the cover from the housing. For example, the cover and walls may include fasteners securing the cover to the housing, or the side walls 9a may include channels toward their upper edges wherein the side peripheral edges of cover 5 are slidably inserted into the channels to engage the walls. Cover 5 has a length slightly less than, and a width substantially the same as, the respective length and width of base 7. It is to be understood that housing 3 may be of any shape or configuration suitable for containing the various interface device components and peripherals described below.

Generally, the side wall 9a disposed adjacent computer system 28 has apertures or openings 15 defined therein to enable communication lines to extend from a processor 44 (FIG. 2) located within interface device 2 to both computer system 28 and foot switch 26. An aperture 15 defined closer to the forward end of the interface device enables a communication line to extend from the interface device to foot switch 26, while the other aperture 15 enables a communication line to extend from the interface device to computer system 28. Apertures 15 may be of any shape or size and may be defined anywhere in housing 3 such that communication lines may be disposed between interface device 2, computer system 28, and foot switch 26 as described above. Similarly, front wall 11 preferably has apertures 17, 19 defined therein for enabling the interface peripherals (i.e., guidewire 4, catheter 6, sheath 8, and syringes 10, 18) to be extended through the interface device interior in order to be manipulated therein from outside the housing for simulation of an interventional radiologic procedure. One aperture 17, defined in front wall 11 toward computer system 28, enables syringe 18 to extend through housing 3, while the other aperture 17, defined toward the middle of front wall 11, enables syringe 10 to extend through the housing such that syringes 10, 18 may each be manipulated from outside the housing. Similarly, an aperture 19, defined in front wall 11 furthest away from computer system 28, enables guidewire 4, catheter 6, and sheath 8 to extend through the housing and be manipulated from outside the housing. Aperture 19 is slightly larger than apertures 17, however, apertures 17, 19 may be of any shape or size and may be defined anywhere in housing 3 capable of permitting the device peripherals to extend through the device housing. Further, the device peripherals may be arranged in any manner capable of permitting their manipulation.

Figure 2:
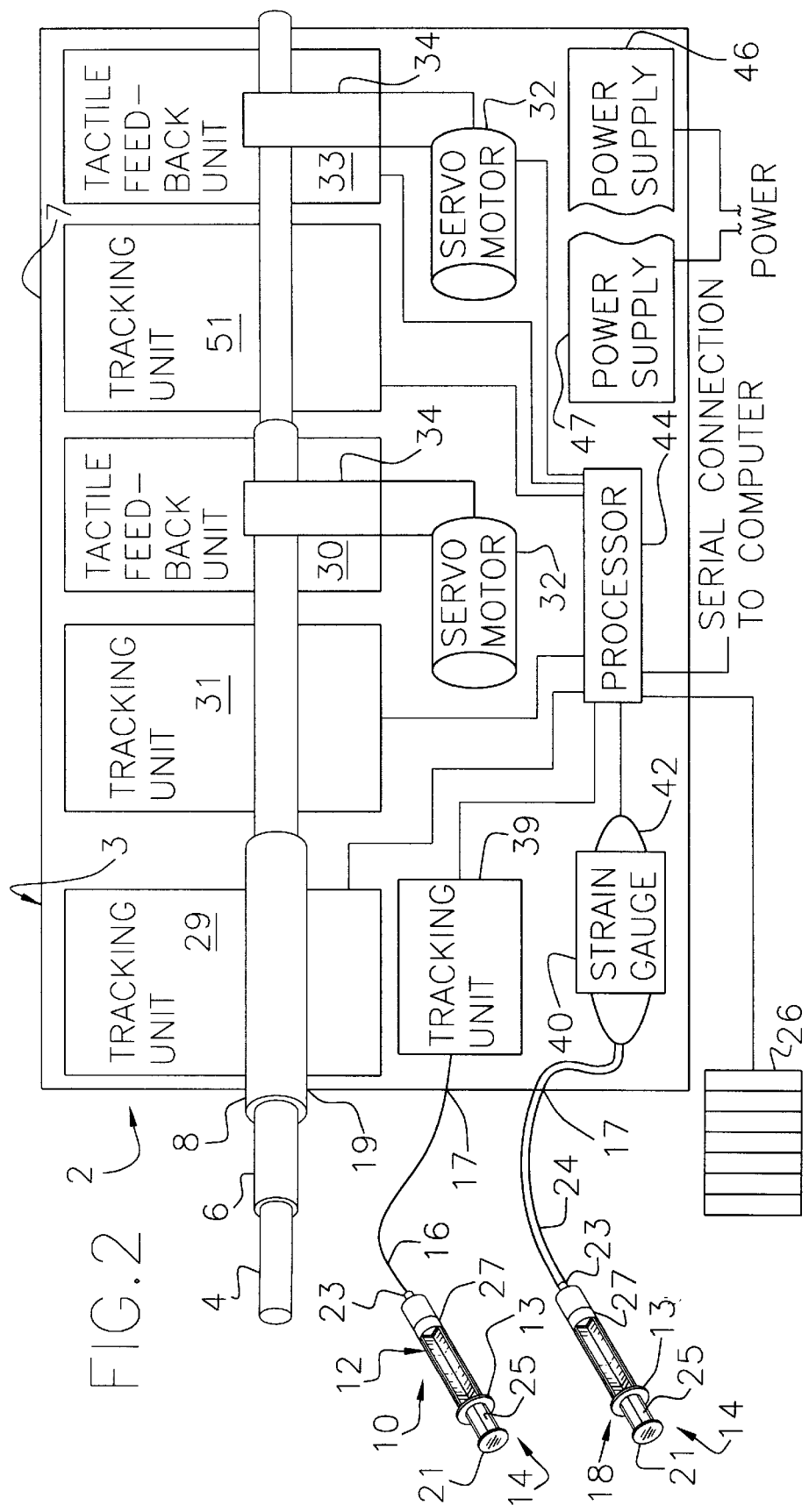
FIG. 2 is a schematic block diagram of an interventional radiology interface device according to the present invention.

Several mock interventional radiologic instruments are disposed at the distal end of interface device 2 to enable performance of various steps of an interventional radiologic procedure by a surgeon. The interface device mock instruments, and components for obtaining instrument measurements and interfacing with computer system 28, are illustrated in FIG. 2. Specifically, interface device 2 includes a guidewire 4, catheter 6, and sheath 8 extending through housing 3 via aperture 19 such that these instruments may be manipulated from outside the housing in order to simulate navigation through an actual arterial anatomy. The guidewire is preferably implemented by a conventional guidewire commonly used in interventional radiologic procedures, and has a length sufficient to traverse the entire length of base 7 and extend externally of housing 3 to enable manipulation of the guidewire from outside the housing during a simulation. Catheter 6 is preferably a conventional catheter commonly used in interventional radiologic procedures having a cross-sectional diameter greater than the cross-sectional diameter of guidewire 4. Catheter 6 further includes an open proximal end and an open distal end such that the guidewire is disposed through the catheter. The catheter has a length substantially similar to the length of base 7, however, the catheter may only extend into interface device 2 for approximately three-fourths the base length such that a sufficient portion of the catheter resides externally of housing 3 to enable manipulation of the catheter from outside the housing during a simulation. Sheath 8 is preferably a conventional sheath of the type commonly used in interventional radiologic procedures having a cross-sectional diameter greater than the cross-sectional diameter of catheter 6. The sheath further includes an open proximal end and an open distal end such that the catheter and guidewire are disposed in and extend entirely through the sheath. Sheath 8 has a length of approximately two thirds the base length, however, the sheath may only extend into the interface device for approximately one-half the base length such that a sufficient portion of the sheath resides externally of housing 3 to enable manipulation of the sheath from outside the housing during a simulation. The guidewire, catheter and sheath partially overlap within, and toward the distal end of, interface device 2 wherein the overlapped portion extends through housing 3. The catheter extends beyond the distal end of the sheath, while the guidewire extends beyond the distal end of the catheter such that each instrument is exposed externally of housing 3 and may be individually manipulated from outside the housing during a simulation procedure. The guidewire, catheter and sheath may be any conventional or commercially available unit, such as model 7.0-40-104423RW manufactured by Cook, Inc., or individual instruments configured as described above.

During an actual medical procedure, each instrument may be withdrawn and exchanged one or more times (e.g., a floppy-tipped guidewire may be exchanged for a torque-able guidewire, the catheter may be exchanged for an angioplasty (balloon-tipped) catheter, and the sheath may be exchanged for a dilator sheath in preparation for deploying a stent). In the simulated procedure, these instrument exchanges are effected by associating a new instrument with an appropriate interface device peripheral (i.e., sheath, catheter, or guidewire) via software selection by mouse or other standard input mechanism. The simulation and associated display thereafter accurately reflect the visual and physical effects of the new instrument.

Guidewire 4, catheter 6 and sheath 8 are manipulated, and an image illustrating the simulated position of these instruments within an internal bodily region of interest (e.g., an arterial network or tree) appears on monitor 56 (FIG. 1). The monitor simulates a fluoroscope display in response to depression of a foot switch 26 substantially similar to foot switches used during interventional radiologic procedures to control a fluoroscope display. Foot switch 26 activates the simulated fluoroscope display to show positions and movement of the guidewire, catheter and sheath, contrast fluid injections, and simulated pharmaceutical action, within an internal bodily region of interest. The foot switch may be implemented by any conventional or commercially available foot switch, such as model T-91-S manufactured by Linemaster Switch Corp. In order to determine the simulated position of the guidewire, catheter and sheath based on their manipulated motion, interface device 2 includes translation and rotation tracking units 29, 31, 51 to measure the translational and rotational movements of the respective sheath, catheter and guidewire. Sheath tracking unit 29 is disposed adjacent sheath 8 within housing 3 toward the distal end of interface device 2 to measure the motion of the sheath, while catheter tracking unit 31 is disposed adjacent catheter 6 within the housing toward the middle of the interface device to measure the motion of the catheter. Catheter tracking unit 31 is disposed in the interface device proximally of the proximal end of sheath 8 such that the catheter extends proximally through the sheath to the catheter tracking unit. Similarly, tracking unit 51 is disposed adjacent guidewire 4 within housing 3 toward the proximal end of the interface device to measure the motion of the guidewire. Guidewire tracking unit 51 is disposed in the interface device proximally of the proximal end of catheter 6 such that the guidewire extends proximally through the catheter to the guidewire tracking unit.

Figure 3:
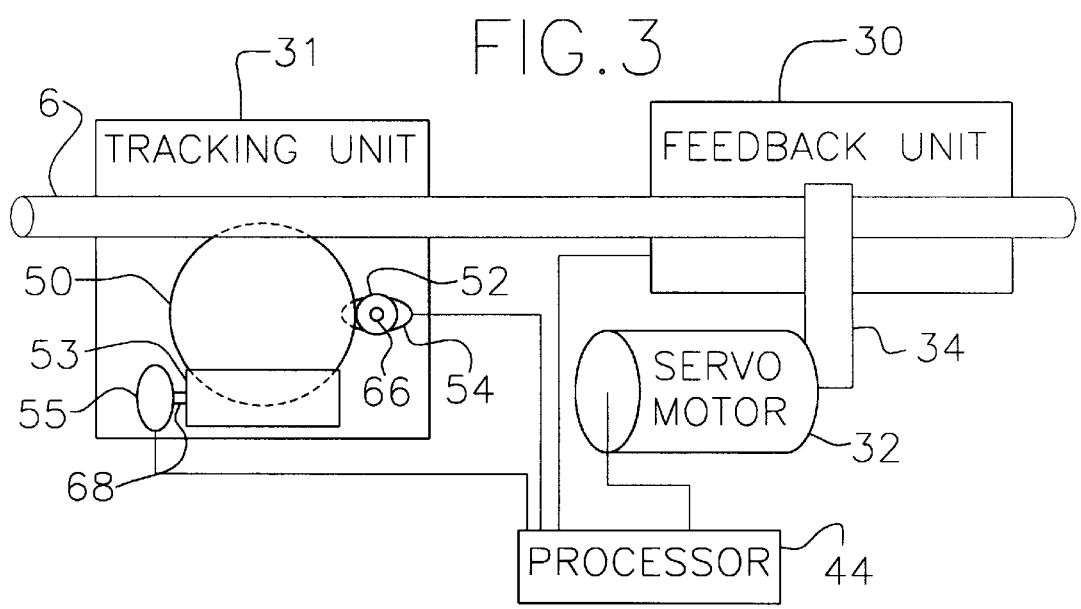
FIG. 3 is a schematic block diagram of a catheter translation and rotation motion tracking unit, and a catheter tactile feedback unit for measuring catheter movement and applying resistive force to the catheter, respectively, according to the present invention.

An exemplary embodiment of a catheter translation and rotation tracking unit 31 is illustrated in FIG. 3. Catheter tracking unit 31 measures the translational and rotational movement of catheter 6 in substantially the same manner utilized to measure movements of a conventional computer mouse, such as the manner utilized in the position control system disclosed in U.S. Pat. No. 3,304,434 (Koster). The disclosure in that patent is expressly incorporated herein by reference in its entirety. Specifically, tracking unit 31 includes a tracking ball 50, rollers 52, 53, shafts 66, 68 and optical encoders 54, 55. Catheter 6 extends through tracking unit 31 and is in frictional relation with tracking ball 50. Tracking ball 50 may be implemented by any conventional or commercially available tracking ball such as model OTIVJ-491980 manufactured by Otiban Corp. Rollers 52, 53 are disposed with their axes orthogonal to each other and in frictional relation with ball 50 such that each roller detects a specific direction component of ball motion corresponding to translation and rotation of catheter 6. Rollers 52, 53 are substantially cylindrical conventional rollers oriented in frictional relation with ball 50 such that the rollers rotate about their respective longitudinal axes in response to tracking ball motion (i.e., catheter motion). Specifically, roller 53 rotates in response to rotation of catheter 6 about its axis; roller 52 rotates in response to longitudinal movement of the catheter along its axis. Shafts 66, 68 have their proximal ends disposed at the distal ends of respective rollers 52, 53, while encoders 54, 55 are respectively disposed at the distal ends of shafts 66, 68. Shafts 66, 68 are typically conventional elongated substantially cylindrical rods having a cross-sectional diameter less than the cross-sectional diameter of respective rollers 52, 53. Shafts 66, 68 are disposed with their longitudinal axes substantially parallel to the longitudinal axes of respective rollers 52, 53. Optical encoders 54, 55 each generate electric pulses corresponding to roller (i.e., catheter) movement. Encoders 54, 55 are preferably optical encoders including a light source, a photodetector and a disk having a plurality of holes or slots circumferentially disposed about the disk with each hole or slot separated by a predetermined angular distance. The encoders may be implemented by any conventional or commercially available optical or other type of encoders, such as model S1-500-IB manufactured by U.S. Digital. Translational movement of catheter 6 causes ball 50 to rotate about an axis substantially parallel to the longitudinal axis of roller 52. Since ball 50 is in frictional relation with roller 52, the rotation of ball 50 about an axis substantially parallel to the longitudinal axis of roller 52 causes roller 52 to rotate. Encoder 54 measures the rotational motion of roller 52, and hence, the translational motion of the catheter. Similarly, rotational movement of catheter 6 causes ball 50 to rotate about an axis substantially parallel to the longitudinal axis of roller 53. Since ball 50 is in frictional relation with roller 53, the rotation of ball 50 about an axis substantially parallel to the longitudinal axis of roller 53 causes roller 53 to rotate. Encoder 55 measures the rotational motion of roller 53, and hence, the rotational motion of the catheter.

As catheter 6 is manipulated, ball 50 rotates in response to the catheter motion, thereby causing rollers 52 and/or 53 to rotate as described above. The rotation of the rollers causes respective shafts 66, 68 to rotate, thereby rotating the respective disks of encoders 54, 55. The encoder disks are generally disposed within each encoder directly in the path between the light source and the photodetector. As each encoder disk rotates, the photodetector within each encoder receives pulses of light from their corresponding light source through the holes or slots in the respective disks. The photodetectors generate electric pulses based on the received light pulses. Since the holes or slots are separated on the disks by a predetermined angular distance, the electric pulses represent an angular displacement of the tracking ball and rollers (i.e., tracking ball and roller motion) and therefore, can be used to measure the corresponding translational and rotational motion of the catheter. Processor 44 (FIG. 2) receives these electric pulses and forwards pulse counts for each encoder to computer system 28 (FIG. 1) wherein the relative position and orientation of the catheter within the internal bodily region of interest (e.g., an arterial network or tree) is determined for display on monitor 56.

Alternatively, tracking unit 31 may measure the translational and rotational motion of catheter 6 via optics without the use of a tracking ball. The tracking of catheter 6 in this fashion is substantially similar to the operation of an optical mouse, such as the optical cursor control device disclosed in U.S. Pat. No. 4,409,479 (Sprague et al) incorporated herein by reference in its entirety. Specifically, the translational and rotational movement of catheter 6 may be measured via use of a grid. The grid is typically constructed of mylar paper and contains a series of orthogonally arranged lines and alternating spaces. The width of the lines is substantially similar to the width of the spaces wherein the lines are typically light absorbent (i.e., non-reflective) while the spaces disposed between the lines are reflective. The grid is typically formed into a cylinder having a cross-sectional diameter slightly greater than the cross-sectional diameter of the catheter such that the catheter extends through the cylinder. Catheter 6 includes a plurality of orthogonally arranged transducers for receiving light reflected from the grid spaces. The grid may be illuminated by a light source disposed on the catheter such that light is reflected by the grid spaces and received by the transducers as the catheter traverses the grid. The light source may also be disposed adjacent the grid to illuminate the grid spaces. As catheter 6 is manipulated through the cylinder, the transducers receive light reflected from the grid, and output an electrical signal (i.e., pulse) proportional to the intensity of the received light.

For the grid approach, translational movement of the catheter is measured by a transducer having a substantially rectangular light detecting area positioned on the catheter with the length of the detecting area (i.e., the longer dimension of the detecting area) substantially perpendicular to the longitudinal axis of the cylinder. The length of the detecting area is substantially similar to the sum of the widths of a line and space (i.e., or any integer multiple of that width sum) such that the transducer continually detects light when the transducer traverses the grid in a direction substantially perpendicular to the cylinder longitudinal axis (i.e., the catheter is rotated). In other words, the transducer produces a substantially continuous unmodulated output in response to rotational motion of the catheter. Conversely, the width of the transducer detecting area is less than the width of a grid line or space such that the transducer does not continually detect light when the transducer traverses the grid in a direction substantially parallel to the cylinder longitudinal axis (i.e., the catheter is translated). The grid lines essentially obstruct the transducer detection area as the catheter traverses the grid lines such that the transducer produces a pulsed output. Since the grid lines and spaces are separated by a predetermined distance, these pulses can be used to measure the translational motion of the catheter.

Still considering the grid approach, rotational movement of the catheter is measured by an additional rotational motion detecting transducer, substantially similar to the translational motion detecting transducer described above, having a substantially rectangular light detecting area positioned on the catheter with the length of the detecting area substantially parallel to the longitudinal axis of the cylinder. The rotational motion detecting transducer generates a continuous unmodulated output in response to translational motion of the catheter in substantially the same manner described above when the transducer traverses the grid in a direction substantially parallel to the longitudinal axis of the cylinder. Further, the rotational motion detecting transducer produces a pulsed output in response to rotational motion of the catheter in substantially the same manner described above when the transducer traverses the grid in a direction substantially perpendicular to the longitudinal axis of the cylinder. The rotational motion detecting transducer essentially detects rotational motion in substantially the same manner described above for the translational motion detecting transducer except that the light detecting area of the rotational motion detecting transducer is oriented orthogonal to the light detecting area of the translational motion detecting transducer. Additional transducers may be added to the catheter to measure additional details of the catheter motion (i.e., direction of translation or rotation) as described in the Sprague U.S. Pat. No. (4,409,479). The transducers may be implemented by any conventional or commercially available photodetectors or optical sensors. It is to be understood that the widths of the grid lines and spaces and the dimensions of the transducer detecting areas are appropriately sized to accommodate the dimensions, and enable tracking of, the catheter. Moreover, tracking units 29, 51 (FIG. 2) are substantially similar to, and function in substantially the same manner as, the exemplary embodiments of tracking unit 31 described above to measure the translational and rotational movements of sheath 8 and guidewire 4, respectively.

In order to simulate the forces encountered by a catheter and guidewire during an actual interventional radiologic procedure, interface device 2 includes tactile feedback units 30, 33 respectively disposed within housing 3 adjacent, and proximal of, tracking units 31, 51. Feedback units 30, 33 simulate forces encountered by a guidewire and catheter during an actual interventional radiologic procedure by applying a resistive force to catheter 6 and guidewire 4, respectively. An exemplary embodiment of tactile feedback unit 30 applying pressure to catheter 6 is illustrated in FIGS. 3–4. Specifically, feedback unit 30 includes load cell 48, pressure application arm 34 and servomotor 32. Catheter 6 is disposed through the feedback unit such that the catheter is disposed between arm 34 and load cell 48. The proximal end of arm 34 is attached to servomotor 32, while the distal end of the arm applies force to catheter 6. Arm 34 is preferably an aluminum machined bar or rod having a substantially perpendicular bend toward its distal end such that force may be applied from the arm to catheter 6 substantially normal to the external catheter surface. Arm 34 is driven by servomotor 32, under control of processor 44, to apply force to catheter 6 and press the catheter against load cell 48. Servomotor 32 may be implemented by any conventional or commercially available servomotor, such as model EO2174 manufactured by Animatics. Computer system 28 (FIG. 1) determines, based on manipulation of catheter 6 and its simulated position within the internal bodily region of interest, the amount of force to apply to the catheter in order to simulate blockages, constrictions and bends in the simulated anatomy (e.g., arterial network or tree). Processor 44 receives control signals from computer system 28 and directs servomotor 32 to apply the proper rotational force (i.e., in the direction of the arrow in FIG. 4) to arm 34 such that the arm transmits the force to catheter 6 and presses the catheter against load cell 48. Load cell 48 detects the pressure exerted on catheter 6 by arm 34 and sends the pressure reading to processor 44. The load cell may be implemented by any conventional or commercially available load cell, such as load cells manufactured by Bertec. Processor 44 implements a feedback control loop to ensure arm 34 applies the appropriate pressure to catheter 6 wherein the pressure reading received from load cell 48 is compared to the desired pressure commanded by computer system 28. In response to the comparison, processor 44 constantly adjusts controls to servomotor 32 such that arm 34 exerts the desired force on catheter 6. The frictional forces resulting from the pressure exerted by arm 34 on catheter 6 (i.e., enhancing or retarding the manipulability of the catheter) impart a realistic feel onto the catheter, thereby providing an enhanced simulation. It is to be understood that feedback unit 33, employed to exert pressure on guidewire 4, is substantially similar to, and functions in substantially the same manner as, feedback unit 30 described above.

Referring back to FIG. 2, interface device 2 further includes a proxy contrast media injection syringe 10 disposed external of housing 3 at the distal end of the interface device for simulating an injection of contrast fluid or other pharmaceutical substance into the internal bodily region of interest. An injection of contrast fluid enables various internal bodily components (e.g., veins, arteries, etc.) to be visible on the display. Syringe 10 is preferably a conventional syringe commonly used in interventional radiologic and other medical procedures, such as model c200 27 BD manufactured by Becton, Dickinson and Co. Syringe 10 typically includes a substantially hollow elongated tubular section 12, and a plunger 14. Tubular section 12 is substantially cylindrical having an open proximal end and a closed distal end with a substantially circular opening defined in the approximate center of the closed distal end. A short projection 23 extends from the substantially circular opening and is typically utilized for connection to an injection port of a catheter or sheath. However, for simulation purposes, projection 23 guides a cable 16 extending from the distal end of plunger 14 through an aperture 17 to injection tracking unit 39 disposed within housing 3 described below. The proximal end of section 12 includes a lip or ledge 13 disposed about the proximal end periphery. Plunger 14 includes an applicator disk 27 disposed at the plunger distal end having a diameter slightly less than the cross-sectional diameter of section 12. The applicator disk is sufficiently thick to permit the disk to expel fluid from the syringe, or for simulation purposes, withstand resistive forces of, and manipulate, cable 16. Plunger 14 further includes a stopper disk 21 disposed at the plunger proximal end, and substantially rectangular panels 25 extending distally from disk 21 to applicator disk 27. Disk 21 has a diameter slightly larger than the cross-sectional diameter of section 12 such that disk 21 acts as a stopper to prevent plunger 14 from becoming trapped within section 12. Panels 25 typically include two substantially rectangular panels having widths slightly less than the cross-sectional diameter of section 12. The panels are positioned orthogonally of each other and intersect along their respective central longitudinal axes (i.e., axes extending between disk 21 and disk 27) to form an 'X' or '+' like configuration. Applicator disk 27 is disposed at the distal end of the panel configuration such that distal movement of plunger 14 forces applicator disk 27 to move distally and manipulate the proximal end of cable 16 disposed on the exterior distal surface of applicator disk 27. The cable is preferably constructed of steel and is substantially similar to cables utilized in bicycle braking systems.

Plunger 14 is disposed within section 12 to permit the plunger to be manipulated in a reciprocating manner within that section. Basically, syringe 10 is preferably manipulated via a single hand by placing the index and middle fingers adjacent the distal surface of lip 13, while the thumb applies pressure to stopper disk 21 to move plunger 14 distally. Stopper disk 21 contacts lip 13 when plunger 14 is in its distalmost position, thereby preventing applicator disk 27 from being pressed against the distal end of section 12. In actual operation during a medical procedure, plunger 14 forces fluid out of section 12 through extension 23, however, for simulation purposes, plunger 14 manipulates cable 16 such that injection tracking unit 39 can measure the motion of syringe 10 to determine a simulated amount of injected fluid.

Syringe 10 may be used to simulate injection of a contrast fluid in order to view an internal bodily region of interest (e.g., veins, arteries, etc.) on a fluoroscope display as in typical interventional radiologic practices. Injection tracking unit 39 measures the manipulation of syringe 10 to determine the amount of fluid injected during the simulation as illustrated in FIGS. 2 and 5. Specifically, the proximal end of cable 16 is disposed at the distal end of plunger 14, while the distal end of cable 16 extends into interface device 2 through an aperture 17 to tracking unit 39. Tracking unit 39 includes a rack gear 36, pinion 38 and optical encoder 41. Optical encoder 41 typically includes a light source, photodetector and a disk having holes or slots circumferentially disposed about the disk with each hole or slot separated by a predetermined angular distance. The optical encoder is substantially similar to, and functions in substantially the same manner as, encoders 54, 55 (FIG. 3) described above except that the encoder disk may be either directly attached to pinion 38, or attached to the pinion by a shaft. Encoder 41 may be implemented by any conventional or commercially available optical or other type of encoder such as model S1-500-IB manufactured by U.S. Digital. Rack 36 is typically a substantially horizontally oriented gear with the distal end of cable 16 disposed at the proximal end of the rack. The rack includes a series of teeth 43 extending downwardly to engage pinion 38. Pinion 38 is preferably disposed beneath rack 36 and is substantially circular with teeth 45 extending outwardly from the circumference of the pinion to engage teeth 43 of rack 36. In other words, teeth 43, 45 are disposed on the respective gear and rack such that the rack teeth interleave the pinion teeth when the rack is translated and/or the pinion is rotated. Alternatively, the rack and pinion may be oriented in any fashion having their respective teeth interleaved as described above to measure the displacement of cable 16. For example, the rack may be disposed beneath the pinion, or the rack may be oriented in a substantially vertical or diagonal orientation with the pinion disposed adjacent the rack.

As plunger 14 is moved distally within section 12, cable 16 is forced to move distally with the plunger. Since the distal end of cable 16 is disposed at the proximal end of rack 36, the cable manipulates the rack relative to pinion 38 depending upon the movement of plunger 14. The movement of rack 36 causes pinion 38 to rotate via the force applied to the pinion from interleaved teeth 43, 45. As pinion 38 rotates, the disk of encoder 41 rotates, thereby enabling the encoder photodetector to receive light pulses in substantially the same manner described above for encoders 54, 55. The photodetector generates electric pulses in response to the received light pulses and sends these electric pulses to processor 44. Since the holes or slots disposed on the encoder disk are separated by a predetermined angular distance, the electric pulses represent the distance rack 36 has manipulated pinion 38, thereby providing an indication of the plunger movement and amount of fluid injected. Processor 44 sends a pulse count to computer system 28 (FIG. 1) such that the computer system can determine the amount of fluid injected. In addition, once the contrast fluid or other pharmaceutical substance is injected via manipulation of syringe 10, depressing foot switch 26 sends a signal via processor 44 to computer system 28 to enable display of the injection on monitor 56.

In order to simulate an angioplasty procedure as described above, interface device 2 further includes a balloon inflation syringe 18 to simulate inflation of an angioplasty balloon disposed at the distal end of a guidewire as illustrated in FIG. 2. Specifically, syringe 18 is substantially similar to contrast media injection syringe 10 described above except that a hose 24 is connected to extension 23. Hose 24 is typically a conventional rubber or plastic hose commonly used in interventional radiologic or other medical procedures. Syringe 18 may be implemented by any conventional or commercially available syringe such as model 197 26 BD manufactured by Becton, Dickinson and Co. Hose 24 extends from extension 23 through an aperture 17 to an angioplasty balloon 42 disposed within housing 3 of interface device 2. Balloon 42 is disposed within a conventional and commercially available pressure sensing sleeve or strain gauge 40. Briefly, the strain gauge includes a band of a sturdy material (e.g., aluminum) formed in the shape of a ring having pressure sensors disposed about the ring. As plunger 14 of syringe 18 is moved distally, disk 27 at the distal end of the inflation syringe plunger 14 forces air or other fluid (e.g., liquid) through hose 24 into balloon 42. Manipulation of plunger 14 inflates balloon 42, thereby enlarging the balloon within pressure sleeve 40. Pressure sleeve 40 measures the pressure exerted on the sleeve by the balloon via the pressure sensors and sends the pressure readings to processor 44. Processor 44 forwards these readings to computer system 28 (FIG. 1) to determine the balloon inflation amount, and display the inflated balloon in the internal bodily region of interest (e.g., arterial network or tree) on monitor 56.

Processor 44 may be implemented by any conventional, commercially available or other processing device, such as model CATCO-RPRE3 manufactured by Animatics. Processor 44 typically polls optical encoders 41 (FIG. 5), 54 (FIG. 3), 55 (FIG. 3), foot switch 26, and pressure sleeve 40 in order to transmit the readings and/or measurements to computer system 28 (FIG. 1). The readings and/or measurements are typically converted into ASCII characters by processor 44 for transmission over a serial communication line to computer system 28. Computer system 28 typically polls processor 44 for the readings and/or measurements in order to update the various positions of (i.e., positions of the guidewire, catheter, sheath, balloon), and implement any functions performed by the interface device peripherals (i.e., fluoroscope display, fluid injection, balloon inflation) on monitor 56. Processor 44 further polls load cell 48 (FIG. 4) in order to control servomotors 32 via a feedback loop to implement feedback resistance as described above. Alternatively, processor 44 may be implemented by a plurality of independent processors (e.g., four) polling specific units and sending the results to computer system 28. For example, two processors may be utilized with each processor implementing the control and feedback loop for a single tactile feedback unit servomotor, while other independent processors may be used to poll the encoders, strain gauge, foot switch and other interface device components. It is to be understood that the processor functions may be assigned to any number of processors in any manner capable of fulfilling the polling requirements.

Power is supplied to interface device 2 via a pair of substantially similar power supplies 46, 47 providing the necessary power for the above described interface device components. The power supplies include a line for receiving electrical power from a standard wall outlet jack and are typically conventional and commercially available power supplies, such as model P24V8A manufactured by Animatics. Power supply 46 is utilized to meet the power requirements of servomotors 32, while power supply 47 provides power to the remaining components of the interface device (e.g., encoders 41, 54, 55, processor 44, strain gauge 40, foot switch 26 etc.). The interface device may include any number of power supplies capable of fulfilling the power requirements of the various interface device components.

Operation of the present invention to perform an exemplary medical procedure is now described with reference to FIGS. 1–2. Specifically, computer system 28 executes a simulation program in accordance with user commands. A particular interventional radiologic procedure, for example an angioplasty procedure, is selected via mouse 62 and/or keyboard 60, while depressing foot switch 26 initiates a fluoroscope display on monitor 56. Guidewire 4, catheter 6 and sheath 8 are manipulated in order to position the simulated guidewire at a blockage point within a simulated arterial tree. The movement of the guidewire, catheter and sheath peripherals is measured as described above to determine and display their positions within the arterial tree on monitor 56. In other words, the position of the guidewire, catheter and sheath is updated on the display based on the movement of the interface guidewire, catheter and sheath peripherals. Since the guidewire, catheter and sheath are often twisted during navigation through an arterial system, feedback units 30, 33 apply proper forces to the catheter and guidewire peripherals, respectively, in order to simulate forces encountered due to blockages, constrictions and bends in the simulated arterial tree as described above. Upon positioning the guidewire at the blockage point within the arterial tree, contrast media injection syringe 10 is manipulated to simulate a contrast fluid injection, while depression of foot switch 26 subsequent to the injection causes the display to show the blockage with the injected fluid diffusing through the arterial tree. The guidewire is now exchanged for a new instrument, typically a stiffer wire as described above, which is then navigated past the blockage via the guidewire peripheral. The catheter is advanced over the guidewire past the lesion to allow further imaging of the lesion via simulated contrast injection. Alternatively, the catheter may be utilized to measure pressure or other characteristics associated with the simulated lesion. The catheter is then typically exchanged for an angioplasty (balloon-tipped) catheter as described above which is then manipulated via the interface device catheter peripheral to position the balloon at the approximate center of the blockage region. Once the balloon is centered in the blockage region, inflation syringe 18 may be manipulated to inflate the angioplasty balloon and open the blockage. The balloon inflation is shown on monitor 56 such that the monitor is utilized to observe successful balloon inflation required to open the blockage without rupturing the artery wall.

It will be appreciated that the embodiments described above and illustrated in the drawings represent only a few of the many ways of implementing an interventional radiology interface apparatus and method according to the principles of the present invention.

The present invention is not limited to the applications described above, but may be utilized to simulate other medical procedures utilizing syringes, guidewires, catheters and/or sheaths (e.g., stent deployment) in substantially the same manner described above. Further, other surgical instruments may be incorporated into the interface device to simulate various other medical procedures in a manner similar to that described above. The medical procedure simulation system computer may be implemented by any computer or processor, preferably of the personal computer type. The interface housing may be of any shape or size, and the front wall may be sloped at any angle. The housing cover may be removably attached to the housing via any conventional or other fastening techniques. The housing apertures may be of any size or shape, and may be defined anywhere in the housing.

The interface device peripherals may be implemented by any medical instruments utilized in medical procedures, and may be disposed in the housing and/or through the apertures in any fashion. Alternatively, the interface device peripherals may be implemented by any computer or other types of input devices to enter data corresponding to medical instrument manipulation into a medical procedure simulation system. The guidewire, catheter, and sheath may be implemented by any conventional guidewire, catheter and sheath or by a series of wire-like members or tubes. The foot switch may be implemented by any conventional foot or other type switch to enable the system display.

The guidewire, catheter and sheath tracking units may be disposed in any manner within the interface device capable of interfacing the guidewire, catheter and sheath. The tracking units may include any type of tracking ball or other device constructed of sufficiently frictional material to interface and convey respective guidewire, catheter and sheath motions. Alternatively, the guidewire, catheter and sheath tracking unit rollers may include sufficiently frictional material to directly interface the guidewire, catheter and sheath to measure their respective motions. The rollers may be oriented on the tracking ball or guidewire, catheter and sheath at any angle to measure any quantity of direction components of motion (e.g., at least one) of the guidewire, catheter and sheath. For example, the rollers may be oriented at an approximate 45° angle relative to the longitudinal axes of the respective guidewire, catheter and sheath whereby each roller may measure both translational and rotational components of motion. The rollers may be of any shape or appropriate size, and may be disposed adjacent any location on the tracking ball or guidewire, catheter and sheath. The shafts interfacing the rollers to the optical encoders may be of any cross-sectional shape, and have any appropriate length. The optical encoders may be implemented by any conventional or other type of encoder or sensor for detecting and measuring translational and rotational motion of the guidewire, catheter and sheath. The encoder disks may include slots, transparent and dark sections, or any other configuration that enables light to be detected by an encoder photodetector to generate electrical pulses. The transducer utilized in the optical embodiment of the guidewire, catheter and sheath tracking units may be implemented by any conventional or other light detector or transducer, and may be disposed on the guidewire, catheter and sheath in any manner to measure any quantity of direction components of motion (e.g., at least one), while the grid may be constructed of any suitable material and may be arranged in any manner with either the lines or spaces emitting or reflecting light. Further, the grid lines and/or spaces may be respectively separated by any suitable distance (i.e., the lines and spaces may include any suitable dimensions).

The guidewire and catheter tactile feedback units may be disposed within the interface device in any manner capable of respectively interfacing the guidewire and catheter. The tactile feedback unit may include any type of servomotor and pressure or force applicator or other devices for applying pressure or force to the guidewire and catheter. Further, the tactile feedback units may include any quantity of clamping, frictional or other types of force application devices (e.g., at least one), such as rollers, to apply force to any quantity of interface device peripherals (e.g., at least one). Moreover, any quantity of force application devices (e.g., at least one) may be utilized to provide force to any quantity of direction components of motion (e.g., at least one) of the interface device peripherals. For example, a tactile force feedback unit may include two force application devices that respectively apply resistance to the translation and rotational components of motion of an interface device peripheral to provide force feedback. The load cell may be implemented by any type of sensor or device capable of measuring pressure or force. The pressure application arm may be of any cross-sectional shape and may include any number (i.e., including zero) of bends having any angle, or may be implemented by any device capable of applying pressure or force to the guidewire and catheter.

The injection syringe may be implemented by any conventional or other type of syringe or other device capable of simulating injections. The injection syringe cable may be implemented by any type of cable or suitably rigid wire type member. The syringe tracking unit and cable may be disposed within the interface device in any manner and may include any type of rack, pinion or other gears, devices or members capable of measuring injection syringe manipulation wherein the gears, devices or members may be disposed, oriented and/or coupled in any manner (e.g., interleaved gears, in frictional relation, etc.). Similarly, the balloon inflation syringe may be implemented by any conventional or other type of syringe or other device capable of inflating an object with any type of fluid (e.g., air, liquid, etc.). The balloon may be implemented by any type of balloon or other inflatable object. The strain gauge may be implemented by any conventional or other type of strain gauge, pressure sleeve, pressure sensor or other type of sensor to measure balloon inflation. The hose extending from the balloon inflation syringe to the balloon may be implemented by any conventional or other type of hose or tube. The balloon, hose and strain gauge may be disposed within the interface device in any manner.

The interface device may include any type or quantity of processors or other circuitry capable of transferring signals between the interface device and medical procedure simulation system computer, and controlling the tactile feedback units. The processor may poll the interface device components recording measurements (e.g., tracking units, tactile feedback units, strain gauge, etc.), or utilize interrupts to initiate signal retrieval from those interface device components. The processor may convert signals to any format for transmission to the medical procedure simulation system computer. The power supplies may be implemented by any type and quantity of power supplies capable of providing adequate power to the interface device.

It is to be understood that the interface device may include any quantity or types of peripherals (e.g., medical instruments) and associated tracking, tactile feedback or other appropriate units to simulate any types of medical procedures on a virtual patient. The guidewire, catheter and sheath components may be utilized in any quantity or combination of components, and may be nested or independently connected to the interface device.

From the foregoing description it will be appreciated that the invention makes available a novel interventional radiology interface apparatus and method wherein an interface device for a medical procedure simulation system interfaces peripherals in the form of mock medical instruments to a medical procedure simulation system computer to enable simulation of a medical procedure.

Having described preferred embodiments for a new and improved interventional radiology interface apparatus and method, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An interface device for use with a simulation system to enable a user to interact with the simulation system to perform a medical procedure on a simulated anatomy of a virtual patient, said interface device comprising:

at least one navigation peripheral capable of selective manipulation by the user and providing navigation information associated with said manipulation to said interface device for transmission to the simulation system for enabling the simulation system to simulate traversal of a corresponding navigation instrument through the simulated anatomy in accordance with said manipulation; and an inflation peripheral selectively manipulable by the user and associated with a navigation instrument balloon disposed at a distal end of a navigation instrument to provide information associated with a balloon inflation level of said navigation instrument balloon resulting from manipulation of said inflation peripheral to said interface device for transmission to the simulation system for enabling the simulation system to simulate incremental inflation of the navigation instrument balloon in accordance with said balloon inflation level and manipulation of said inflation peripheral.

2. The device of claim 1 further including at least one navigation peripheral tracking unit associated with said at least one navigation peripheral to measure manipulation of that navigation peripheral.

3. The device of claim 1 further including:

at least one tactile feedback unit associated with a corresponding navigation peripheral to apply force to that navigation peripheral to simulate forces encountered by the corresponding navigation instrument during a medical procedure.

4. The device of claim 3 further including a processor to control each tactile feedback unit to apply a force to said corresponding navigation peripheral corresponding to forces encountered by the corresponding navigation instrument during a medical procedure, and each tactile feedback unit includes:

a force applicator disposed proximate said corresponding navigation peripheral to apply force to said corresponding navigation peripheral; and a force sensor to measure the force applied by said force applicator to said corresponding navigation peripheral;

wherein said processor is responsive to force measurement from said force sensor to control said force applicator.

5. An interface device for use with a simulation system to enable a user to interact with the simulation system to perform a medical procedure on a simulated anatomy of a virtual patient, said interface device comprising:

at least one navigation peripheral capable of selective manipulation by the user and providing navigation information associated with said manipulation to said interface device for transmission to the simulation system for enabling the simulation system to simulate traversal of a corresponding navigation instrument through the simulated anatomy in accordance with said manipulation;

an inflation peripheral selectively manipulable by the user and associated with a navigation instrument balloon disposed at a distal end of a navigation instrument to provide information associated with manipulation of said inflation peripheral to said interface device for transmission to the simulation system for enabling the simulation system to simulate inflation of the navigation instrument balloon in accordance with manipulation of said inflation peripheral; and an injection peripheral selectively manipulable by the user to provide injection information associated with manipulation of said injection peripheral to said interface device for transmission to the simulation system to enable the simulation system to simulate injection of fluids within the simulated anatomy in accordance with manipulation of said injection peripheral.

6. The device of claim 5 further including a foot switch to control a simulation system display.

7. The device of claim 5 wherein said injection peripheral includes an injection syringe, and said interface device further includes a syringe tracking unit to measure manipulation of said injection syringe.

8. An interface device for use with a simulation system to enable a user to interact with the simulation system to perform a medical procedure on a simulated anatomy of a virtual patient, said interface device comprising:

a plurality of arterial network navigation peripherals each selectively manipulable by the user and associated with a corresponding arterial network navigation instrument to provide navigation information associated with manipulation of that navigation peripheral to said interface device for transmission to the simulation system for enabling the simulation system to simulate simultaneous navigation of said corresponding arterial network navigation instruments through an arterial network of the simulated anatomy in accordance with manipulation of said associated navigation peripherals.

9. An interface device for use with a simulation system to enable a user to interact with the simulation system to perform a medical procedure on a simulated anatomy of a virtual patient, said interface device comprising:

a plurality of navigation peripherals each selectively manipulable by the user and providing navigation information associated with manipulation of that navigation peripheral to said interface device for transmission to the simulation system for enabling the simulation system to simulate traversal of a corresponding navigation instrument through the simulated anatomy in accordance with manipulation of that navigation peripheral, wherein said plurality of navigation peripherals includes:

a guidewire to provide said navigation information associated with manipulation of said guidewire to said interface device for transmission to the simulation system for enabling the simulation system to simulate traversal of a corresponding guidewire instrument through the simulated anatomy in accordance with manipulation of said guidewire;

a catheter to provide said navigation information associated with manipulation of said catheter to said interface device for transmission to the simulation system for enabling the simulation system to simulate traversal of a corresponding catheter instrument through the simulated anatomy in accordance with manipulation of said catheter; and a sheath to provide said navigation information associated with manipulation of said sheath to said interface device for transmission to the simulation system for enabling the simulation system to simulate traversal of a corresponding sheath instrument through the simulated anatomy in accordance with manipulation of said sheath.

10. The device of claim 9 further including:

an inflation peripheral selectively manipulable by the user and associated with a navigation instrument balloon disposed at a distal end of a navigation instrument to provide information associated with manipulation of said inflation peripheral to said interface device for transmission to the simulation system for enabling the simulation system to simulate inflation of the navigation instrument balloon in accordance with manipulation of said inflation peripheral.

11. An interface device for use with a simulation system to enable a user to interact with the simulation system to perform a medical procedure on a simulated anatomy of a virtual patient, said interface device comprising:

an inflation peripheral selectively manipulable by the user and associated with a navigation instrument balloon disposed at a distal end of a navigation instrument to provide information associated with a balloon inflation level of said navigation instrument balloon resulting from manipulation of said inflation peripheral to said interface device for transmission to the simulation system for enabling the simulation system to simulate incremental inflation of the navigation instrument balloon in accordance with said balloon inflation level and manipulation of said inflation peripheral.

12. An interface device for use with a simulation system to enable a user to interact with the simulation system to perform a medical procedure on a simulated anatomy of a virtual patient, said interface device comprising:

at least one navigation peripheral selectively manipulable by the user and providing navigation information associated with manipulation of that navigation peripheral to said interface device for transmission to the simulation system to enable the simulation system to simulate traversal of a corresponding navigation instrument through the simulated anatomy in accordance with said manipulation;

at least one tactile feedback unit wherein each tactile feedback unit is associated with a corresponding navigation peripheral to apply force to that navigation peripheral to simulate forces encountered by the corresponding navigation instrument during a medical procedure; and a processor to control each tactile feedback unit to apply a force to said corresponding navigation peripheral corresponding to forces encountered by the corresponding navigation instrument during a medical procedure, wherein said processor controls each tactile feedback unit in response to the simulation system determining said force to apply to said corresponding navigation peripheral, and each tactile feedback unit includes:

a force applicator disposed proximate said corresponding navigation peripheral to apply force to said corresponding navigation peripheral; and a force sensor to measure the force directly applied by said force applicator to said corresponding navigation peripheral and to provide said force measurement to said processor;

wherein said processor controls said force applicator to apply said force determined by the simulation system to said corresponding navigation peripheral by adjusting force applied by said force applicator to said corresponding navigation peripheral based on the force measurement from said force sensor.

13. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing at least one navigation peripheral to the interface device, said at least one navigation peripheral being selectively manipulable by the user and associated with a corresponding navigation instrument;

(b) interfacing an inflation peripheral to the interface device wherein the inflation peripheral is selectively manipulable by the user and associated with a navigation instrument balloon disposed at a distal end of a navigation instrument;

(c) measuring manipulation of each navigation peripheral and the inflation peripheral via the interface device, wherein the measured manipulation of the inflation peripheral provides information associated with a balloon inflation level of the navigation instrument balloon resulting from manipulation of the inflation peripheral;

(d) transmitting the manipulation measurement for said at least one navigation peripheral from the interface device to the simulation system to enable the simulation system to simulate traversal of the corresponding navigation instrument associated with said at least one navigation peripheral through the simulated anatomy in accordance with manipulation of that navigation peripheral; and (e) transmitting the manipulation measurement for the inflation peripheral from the interface device to the simulation system to enable the simulation system to simulate incremental inflation of the navigation instrument balloon in accordance with the balloon inflation level and manipulation of the inflation peripheral.

14. The method of claim 13 further including the step of:

(f) applying force to a corresponding navigation peripheral to simulate forces encountered by the corresponding navigation instrument during a medical procedure.

15. The method of claim 14 wherein step (f) further includes the steps of:

(f.1) disposing a force applicator proximate the corresponding navigation peripheral;

(f.2) applying force to the corresponding navigation peripheral via the force applicator;

(f.3) measuring the force applied by the force applicator to the corresponding navigation peripheral via a force sensor; and (f.4) controlling the force applicator based on the force measurement.

16. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing at least one navigation peripheral to the interface device, said at least one navigation peripheral being selectively manipulable by the user and associated with a corresponding navigation instrument;

(b) interfacing an inflation peripheral to the interface device wherein the inflation peripheral is selectively manipulable by the user and associated with a navigation instrument balloon disposed at a distal end of a navigation instrument;

(c) measuring manipulation of each navigation peripheral and the inflation peripheral via the interface device;

(d) transmitting the manipulation measurement for said at least one navigation peripheral from the interface device to the simulation system to enable the simulation system to simulate traversal of the corresponding navigation instrument associated with said at least one navigation peripheral through the simulated anatomy in accordance with manipulation of that navigation peripheral;

(e) transmitting the manipulation measurement for the inflation peripheral from the interface device to the simulation system to enable the simulation system to simulate inflation of the navigation instrument balloon in accordance with manipulation of the inflation peripheral;

(f) interfacing an injection peripheral selectively manipulable by the user to the interface device;

(g) measuring manipulation of the injection peripheral via the interface device; and (h) transmitting the manipulation measurement for the injection peripheral from the interface device to the simulation system to enable the simulation system to simulate injection of fluids within the simulated anatomy in accordance with manipulation of the injection peripheral.

17. The method of claim 16 further including the step of:

(i) interfacing a foot switch to the simulation system via the interface device to control a simulation system display.

18. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing a plurality of arterial network navigation peripherals to the interface device wherein each arterial network navigation peripheral is selectively manipulable by the user and associated with a corresponding instrument for navigating through an arterial network;

(b) measuring manipulation of each arterial network navigation peripheral via the interface device; and (c) transmitting the manipulation measurement for each arterial network navigation peripheral from the interface device to the simulation system to enable the simulation system to simulate simultaneous navigation of the corresponding arterial network navigation instruments through an arterial network of the simulated anatomy in accordance with manipulation of the associated arterial network navigation peripherals.

19. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing a plurality of navigation peripherals in the form of a guidewire, catheter and sheath to the interface device wherein each navigation peripheral is selectively manipulable by the user and associated with a corresponding navigation instrument;

(b) measuring manipulation of the guidewire, catheter and sheath via the interface device; and (c) transmitting the manipulation measurements for the guidewire catheter and sheath from the interface device to the simulation system to enable the simulation system to respectively simulate traversal of corresponding guidewire, catheter and sheath instruments through the simulated anatomy in accordance with manipulation of the guidewire, catheter and sheath.

20. The method of claim 19 further including the steps of:

(d) interfacing an inflation peripheral to the interface device wherein the inflation peripheral is selectively manipulable by the user and associated with a navigation instrument balloon disposed at a distal end of a navigation instrument;

(e) measuring manipulation of the inflation peripheral via the interface device; and (f) transmitting the manipulation measurement for the inflation peripheral from the interface device to the simulation system to enable the simulation system to simulate inflation of the navigation instrument balloon in accordance with manipulation of the inflation peripheral.

21. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing an inflation peripheral to the interface device wherein the inflation peripheral is selectively manipulable by the user and associated with a navigation instrument balloon disposed at a distal end of a navigation instrument;

(b) measuring manipulation of the inflation peripheral via the interface device, wherein the measured manipulation of the inflation peripheral provides information associated with a balloon inflation level of the navigation instrument balloon resulting from manipulation of the inflation peripheral; and (c) transmitting the manipulation measurement for the inflation peripheral from the interface device to the simulation system to enable the simulation system to simulate incremental inflation of the navigation instrument balloon in accordance with the balloon inflation level and manipulation of the inflation peripheral.

22. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing at least one navigation peripheral to the interface device wherein each navigation peripheral is selectively manipulable by the user and associated with a corresponding navigation instrument;

(b) measuring manipulation of each navigation peripheral;

(c) transmitting the manipulation measurement for each navigation peripheral from the interface device to the simulation system to enable the simulation system to simulate traversal of the corresponding navigation instrument associated with each navigation peripheral through the simulated anatomy in accordance with manipulation of each navigation peripheral; and (d) applying force to a corresponding navigation peripheral to simulate forces encountered by the corresponding navigation instrument during a medical procedure, wherein the force applied to the corresponding navigation peripheral is determined by the simulation system, and step (d) further includes:

(d.1) disposing a force applicator proximate the corresponding navigation peripheral;

(d.2) applying force to the corresponding navigation peripheral via the force applicator;

(d.3) measuring the force directly applied by the force applicator to the corresponding navigation peripheral via a force sensor; and (d.4) controlling the force applicator to apply the force determined by the simulation system to the corresponding navigation peripheral by adjusting force applied by the force applicator to the corresponding navigation peripheral based on the force measurement from the force sensor.

23. An interface device for use with a simulation system to enable a user to interact with the simulation system to perform a medical procedure on a simulated anatomy of a virtual patient, said interface device comprising:

an injection peripheral selectively manipulable by the user to provide injection information associated with an amount of manipulation of said injection peripheral and a quantity of injected fluid resulting from said manipulation to said interface device for transmission to the simulation system to enable the simulation system to simulate injection of fluids within the simulated anatomy in accordance with said quantity of injected fluid and manipulation of said injection peripheral.

24. A method to enable a user to interact with a simulation system via an interface device to perform a medical procedure on a simulated anatomy of a virtual patient, wherein the interface device interfaces user manipulable peripherals to the simulation system, said method comprising the steps of:

(a) interfacing an injection peripheral selectively manipulable by the user to the interface device;

(b) measuring manipulation of the injection peripheral via the interface device, wherein the measured manipulation of the injection peripheral provides information associated with a quantity of injected fluid resulting from manipulation of the injection peripheral; and (c) transmitting the manipulation measurement for the injection peripheral from the interface device to the simulation system to enable the simulation system to simulate injection of fluids within the simulated anatomy in accordance with the quantity of injected fluid and manipulation of the injection peripheral.

* * * * *